United States Patent [19]
Bowman

[11] Patent Number: 5,168,759
[45] Date of Patent: Dec. 8, 1992

[54] STRAIN GAUGE FOR MEDICAL APPLICATIONS

[75] Inventor: Bruce R. Bowman, Eden Prairie, Minn.

[73] Assignee: EdenTec, Eden Prairie, Minn.

[21] Appl. No.: 751,507

[22] Filed: Aug. 29, 1991

[51] Int. Cl.⁵ .............................................. G01B 7/16
[52] U.S. Cl. ...................................... 73/775; 29/595
[58] Field of Search ............... 73/862.65, 782, 767, 73/775, 776, 774; 29/595

[56] References Cited

U.S. PATENT DOCUMENTS

| | | | |
|---|---|---|---|
| 3,118,301 | 1/1964 | Bajenski et al. | 73/774 |
| 3,782,182 | 1/1974 | Starr | 73/782 |
| 5,079,535 | 1/1992 | Neuman et al. | 338/2 |

Primary Examiner—Jerry W. Myracle
Attorney, Agent, or Firm—James R. Shay; John L. Rooney

[57] ABSTRACT

A strain gauge and method of making same for use in certain medical applications, such as sensing the occurrence of an apnea event. The device is also applicable to monitoring mechanical motion associated with other medical conditions. The strain gauge actually measures the change in direct current resistance produced by stretching and compression of a number of carbon deposits coupled in series on a longitudinally extendible substrate. This extendibility is produced by suitably die cutting a flexible but inherently inelastic insulative substrate. The easily produced device may be used externally or encapsulated for implantation.

10 Claims, 10 Drawing Sheets

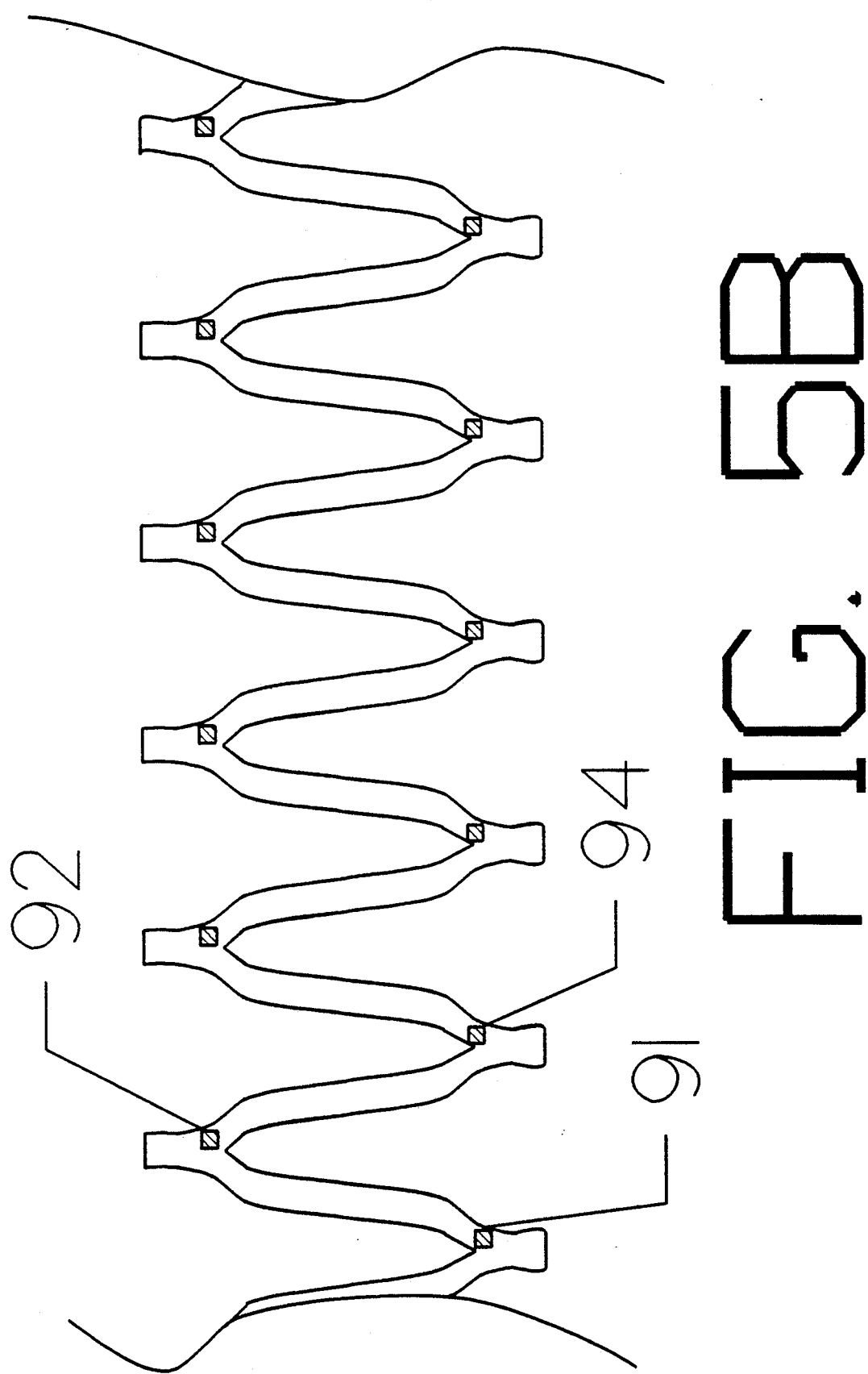

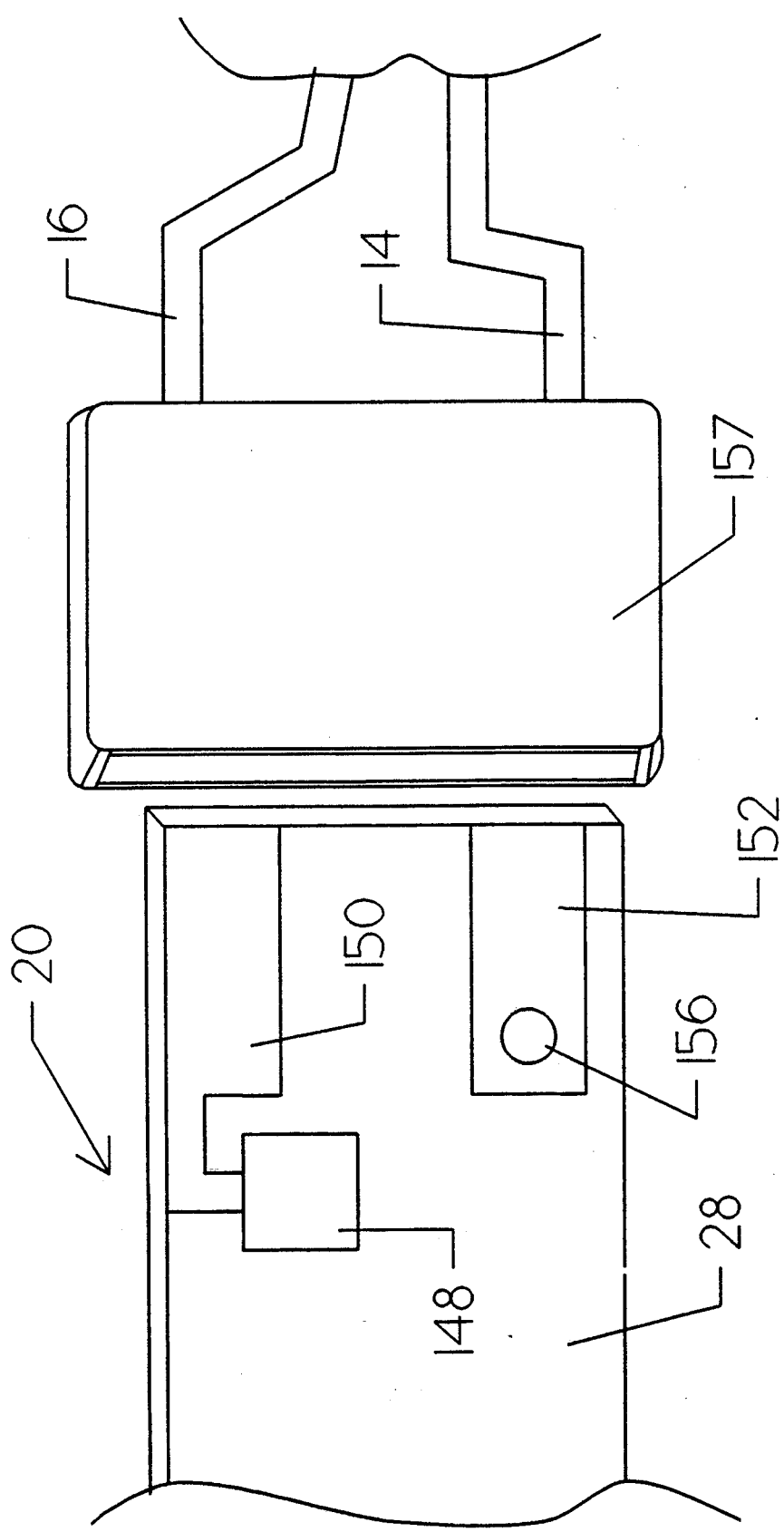

STRAIN GAUGE FOR MEDICAL APPLICATIONS

CROSS REFERENCE TO CO-PENDING APPLICATIONS

U.S. patent application Ser. No. 665,552, filed Mar. 5, 1991, entitled "Flow Sensor System", is assigned to the assignee of the present invention and is incorporated herein by reference.

BACKGROUND OF THE INVENTION

1. Field of the Invention

The present invention relates generally to strain gauges and more particularly relates to strain gauges for medical applications.

2. Description of the Prior Art

It is desirable with a number of medical devices to measure mechanical motion. This is particularly true with regard to monitoring patients susceptible to apnea, or cessation of respiration. However, a number of other applications are readily apparent, such as monitoring cardiac activity, joint angles, joint motion, muscle or penile tumescence, etc.

Most frequently, direct monitoring of the mechanical motion is sufficiently difficult that the desired motion is monitored using an indirect measurement technique. Perhaps the most common is found in cardiac pacing wherein it is common to sense electrical activity of the myocardium and associate that with the presence or absence of the actual mechanical activity.

Such indirect monitoring is particularly prevalent in the treatment of respiratory diseases including apnea. Acoustic sensors for monitoring respiration are seen in U.S. Pat. No. 4,602,644 issued to DeBenedetto et al., and U.S. Pat. No. 4,595,016 issued to Fertig et al. Optoelectric flow sensors are described by Dietz in U.S. Pat. Nos. 4,878,502 and 4,745,925.

Other indirect monitoring techniques include gas monitoring in U.S. Pat. No. 4,366,821 issued to Wittmaier et al., and moisture sensing using a sodium chloride crystal as found in U.S. Pat. No. 4,326,404 issued to Mehta. U.S. Pat. No. 4,306,867 issued to Krasner shows the use of a pressure sensor. An impedance plethysmograph is employed in U.S. Pat. No. 4,289,142 issued to Kearns. The use of thermoresistive sensors is suggested in U.S. Pat. No. 3,903,876 issued to Harris; U.S. Pat. No. 3,884,219 issued to Richardson et al; and U.S. Pat. No. 3,999,537 issued to Noiles.

The preferred method of measuring mechanical activity directly is through the use of a strain gauge. The term strain gauge is typically used in the art to refer to such a device even though they tend to measure mechanical displacement rather than strain. Perhaps the term is more appropriately applied when the device monitors a mechanical spring within its elastic limits, wherein the measurement of distension or compression can readily be correlated to strain on the components of the mechanical spring.

Many strain gauges utilize the mechanical changes to vary the capacitive or inductive impedance of an alternating current path. This technique tends to provide a sensor element which is easily constructed. However, the electronic circuitry associated with such systems tends to be very complex. To simplify the electronics, strain gauges which vary direct current resistance with mechanical motion have been developed. U.S. Pat. No. 4,971,065 issued to Pearce shows such a system. However, these devices tend to have a rather poor signal-to-noise ratio because of the high resistivity of the overall sensor generated by the relatively long serpentine low conductivity path needed to generate sufficient resistance change to monitor the desired motion.

SUMMARY OF THE INVENTION

The present invention overcomes the disadvantages found in the prior art by providing a strain gauge which directly measures mechanical movement. The device operates by monitoring simple changes in direct current resistance, which greatly minimizes the complexity of the electronic circuitry. The device is easily fabricated for disposable use or may be encapsulated for chronic implantable applications.

The basic sensor is fabricated on a thin flexible but inelastic substrate of a convenient insulative material. This structure may be adhesively or otherwise bonded to an elastic backing which is coupled to the patient using a belt or other attachment means for external applications. The ends of the basic sensor are fixedly attached to an elastic encapsulating tube of silicone rubber or other biocompatible material for implantable use.

A serpentine conductor of silver or other highly conductive material is silk screened or otherwise deposited on the substrate. This conductor is placed in such a manner as to have a number of breaks in the conduction path. These breaks are electrically coupled using a deposited material of lower conductivity, such as graphite.

The substrate is die cut to permit longitudinal expansion by deforming the areas having the deposited lower conductivity material. Depending upon the geometry of the breaks, longitudinal expansion can be made to cause either compression or distension at the areas of lower conductivity. Because each of the deformed areas is electrically resistive, relatively large changes in resistance result from the distension or compression caused by relatively small extensions in the longitudinal direction. However, most of the distance of the serpentine electrical circuit pathway through the sensor consists of a highly conductive material. Therefore, the total resistance of the pathway is kept lower than systems employing the resistive material for the entire length of the pathway.

The high inherent signal-to-noise ratio of a sensor made in accordance with the present invention permits simplification of the signal processing circuitry. This is particularly pronounced because of the relatively low impedance of the strain gauge device.

For chronic implantable use, the sensor substrate is packaged in an elastic biocompatible material, such as silicone rubber. In this packaging technique, the substrate is placed within a tube of the biocompatible material. The ends of the sensor substrate are fixedly attached to the ends of the tube, which are sealed against the ingress of bodily fluids. As the biocompatible tube stretches and compresses, the sensor substrate within also expands and contracts in the longitudinal dimension.

BRIEF DESCRIPTION OF THE DRAWINGS

Other objects of the present invention and many of the attendant advantages of the present invention will be readily appreciated as the same becomes better understood by reference to the following detailed description when considered in connection with the accompa

FIG. 5B is a schematic view of the sensor substrate as fully extended;

FIG. 6 is a closeup view showing the terminal connector;

DETAILED DESCRIPTION OF THE PREFERRED EMBODIMENTS

Figure 1:
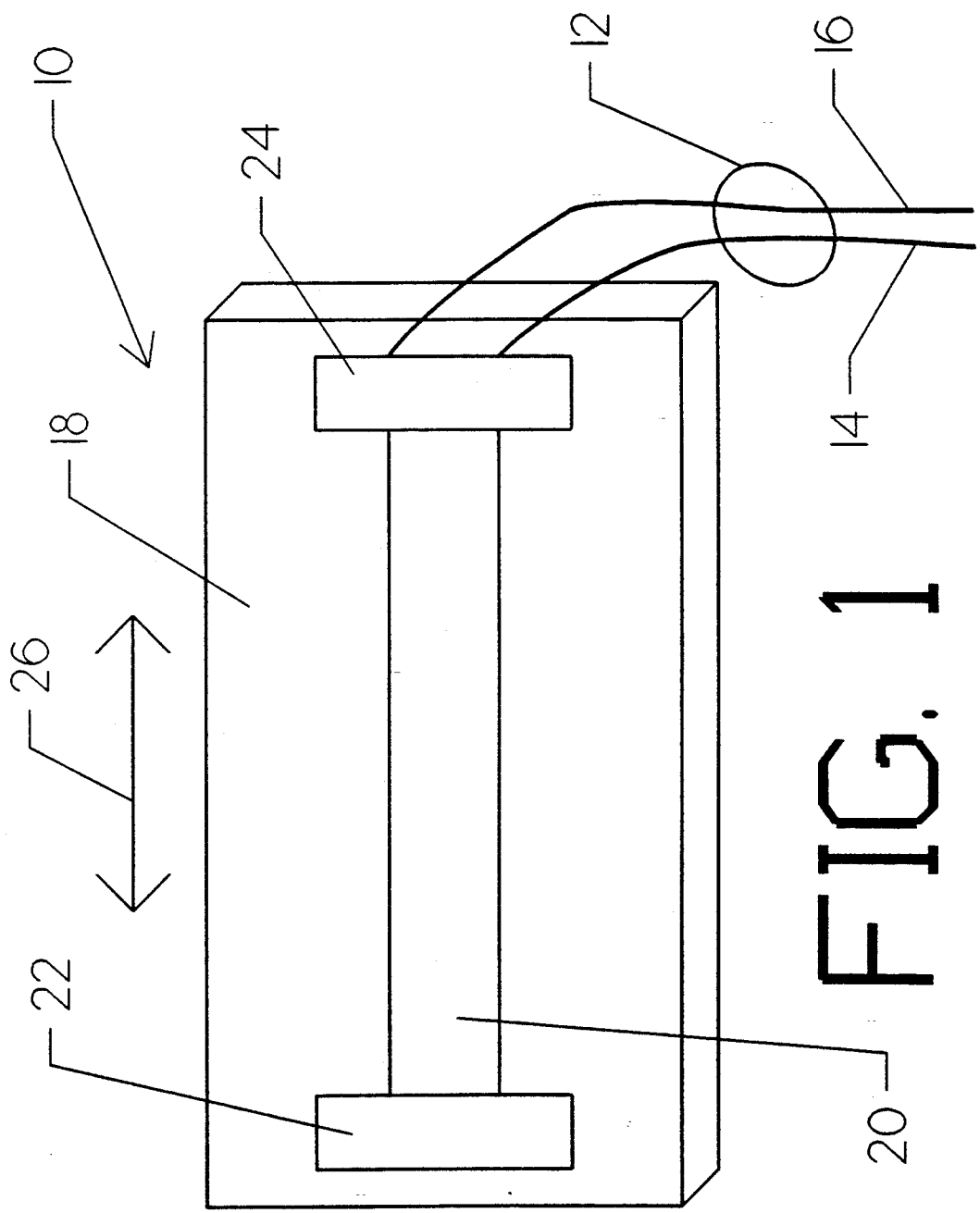
- FIG. 1 is a view of the strain gauge sensor as packaged for external use.

FIG. 1 is a simplified view of strain gauge 10 as packaged for disposable use in an acute external application such as apnea monitoring. The ends of basic sensor structure 20 are applied to acute substrate 18 using adhesive bonds 22 and 24. Acute substrate 18 is chosen to be soft and flexible. Various polymer foams are readily available for this use. It must be elastic in the longitudinal dimension, such that it is free to stretch and compress in the directions shown by arrow 26. Acute substrate 18 may be removably attached to an apnea patient (not shown) using a belt, adhesive, or other convenient means.

Because basic sensor structure 20 is fixedly attached to acute substrate 18, it must also be extendible and compressible in the directions of arrow 26. To permit some compression, basic sensor structure 20 must be placed under some slight tension at the time of fixation to acute substrate 18. This will become apparent from the discussion below concerning the construction of basic sensor structure 20.

The surface of basic sensor structure 20 having the resistive elements which change with mechanical movement is placed adjacent to acute substrate 18. The surface of basic sensor structure 20 facing away from the patient contains only a return circuit path. This conductor of low resistivity permits both wire 14 and wire 16, comprising cable 12, to exit basic sensor structure 20 from the same side of basic sensor structure 20. Note that this means that basic sensor structure 20 is a multi-sided substrate.

Figure 2:
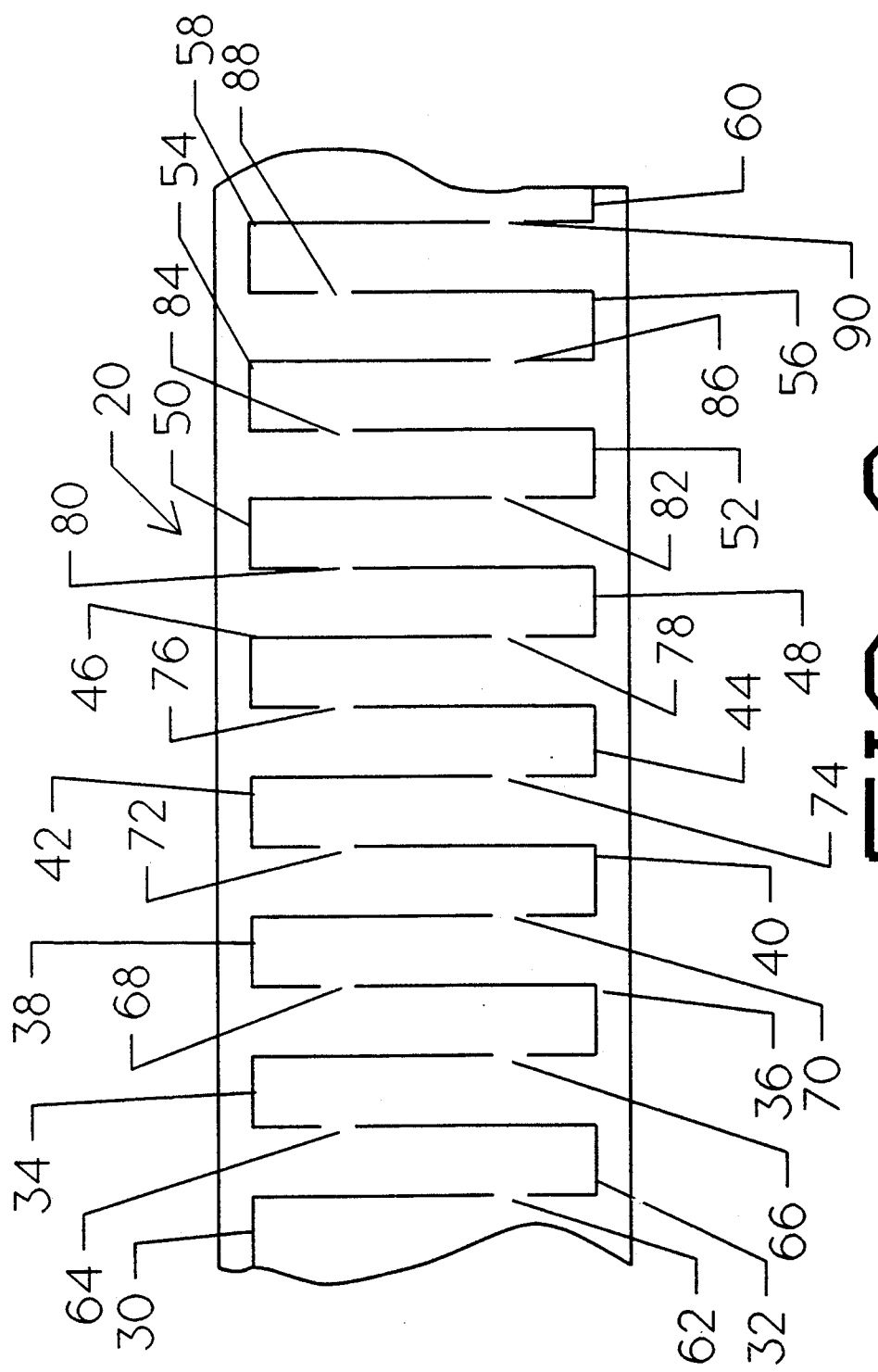
FIG. 2 is a view of the substrate after application of the highly conductive path.

FIG. 2 shows the initial steps of fabricating basic sensor structure 20. Sensor substrate 28 is a flexible insulator. The flexibility permits basic sensor structure 20 to readily conform to the body of the patient after attachment to acute substrate 18. However, unlike acute substrate 18, sensor substrate 28 is not elastic in the longitudinal dimension. This property ensures that as basic sensor structure 20 is stretched and compressed, the stretching and compression will occur primarily at specific desired areas.

A serpentine conductor, comprising segments 30, 32, 34, 36, 38, 40, 42, 44, 46, 50, 52. 54, 56, 58, and 60, is placed on one surface of sensor substrate 28. Preferably, these segments are placed using a silk screening process of conductive ink. The preferred conductive ink for this purpose has a high silver content to make each segment highly conductive. Alternatively, the segments may be deposited using any other convenient process.

Breaks 62, 64, 66, 68, 70, 72, 74, 76, 78, 80, 82, 84, 86, 88, and 90 separate each of the respective segments and represent breaks in the conductive path of the serpentine conductor. It is important that a high proportion of the total length of the serpentine path be highly conductive and that the sum total of the longitudinal dimension of the breaks be small in relation thereto.

Figure 3:
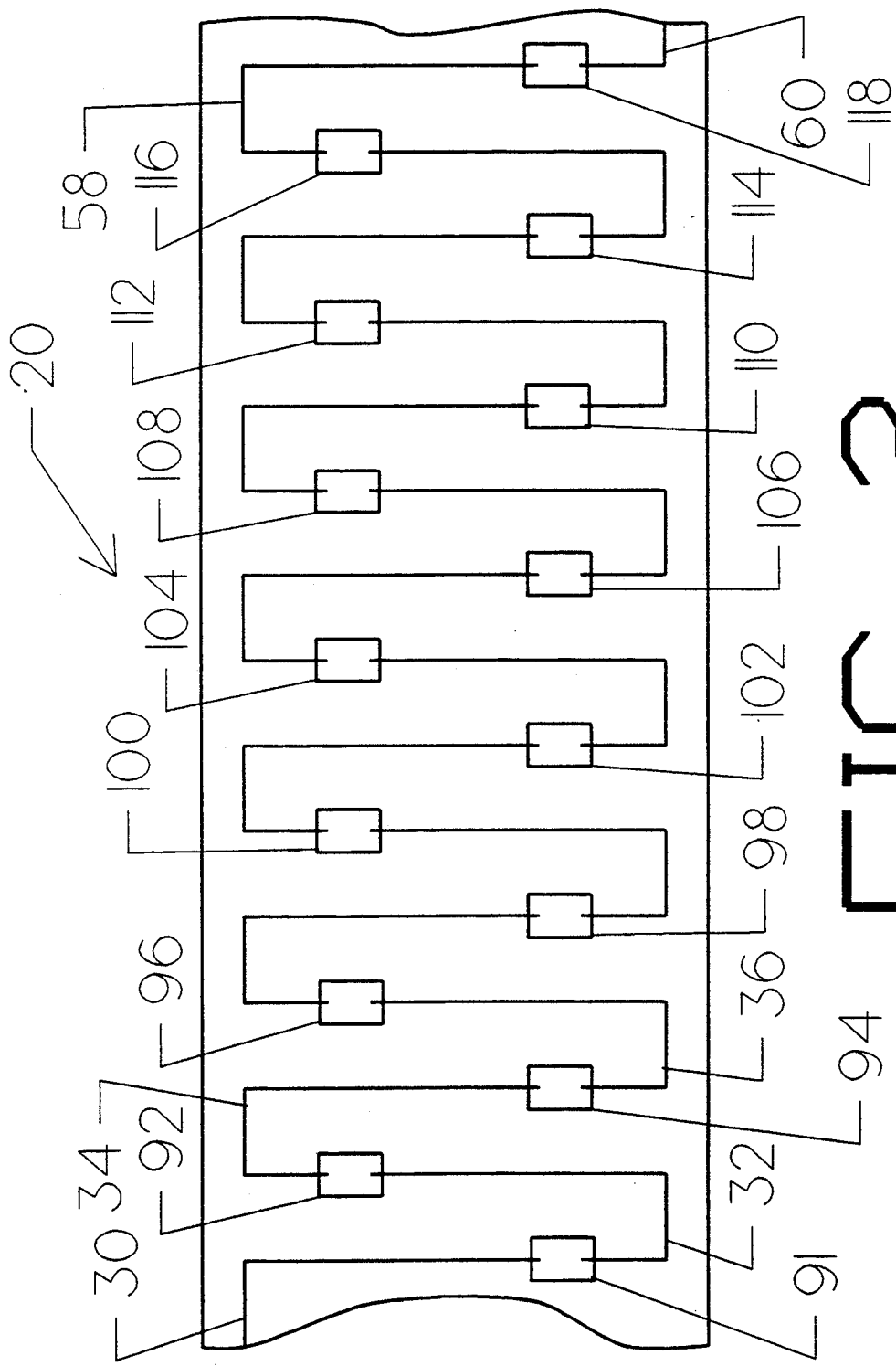
FIG. 3 is a view similar to FIG. 2 showing positioning of the resistive areas.

FIG. 3 is similar to FIG. 2 after the addition of the areas of resistive material. At each of the breaks 62-90, a layer of graphite or other relatively high resistance material is deposited to complete the electrical contact between adjacent ones of segments 30-60. This results in resistive pads 91, 92, 94, 96, 98, 100, 102, 104, 106, 108, 110, 112, 114, 116, and 118. At this point in the fabrication process, there is electrical conductivity from segment 30 to segment 60 through the serpentine conductor. Most of the linear distance between segment 30 and segment 60 is via the highly conductive segments, however, even though the total linear distance of breaks 62-90 is small, the relative resistance of the breaks is high and the overall impedance of basic sensing structure 20 is high.

Figure 4:
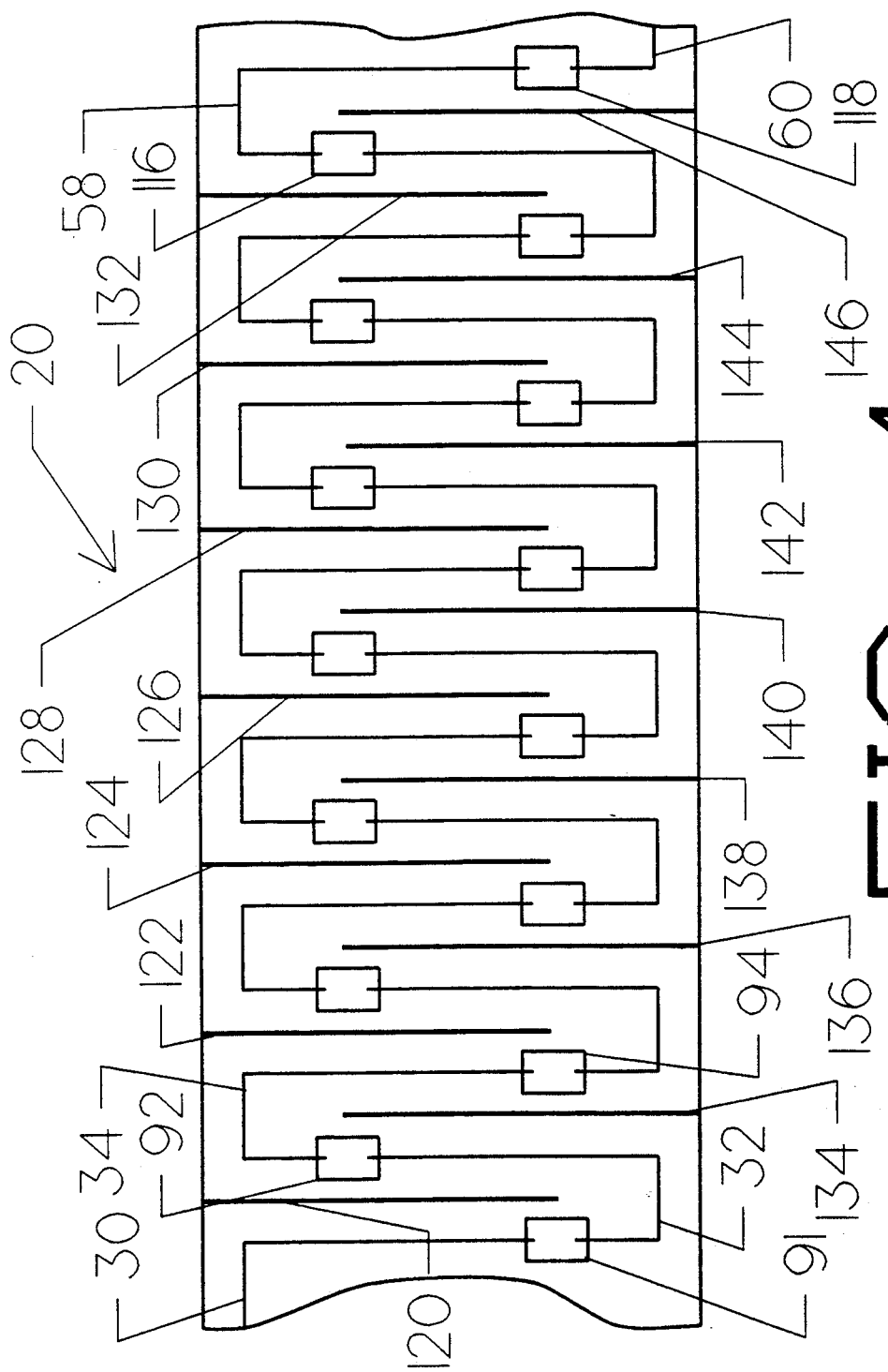
FIG. 4 is a view similar to FIG. 3 showing the location of the die cuts.

FIG. 4 is a view similar to FIG. 3 after die cutting. Because sensor substrate 28 is inelastic, it would not appreciably stretch or compress in the longitudinal direction with mechanical motion. To permit the desired change in longitudinal dimension, sensor substrate 28 is die cut along cut lines 120, 122, 124, 126, 128, 130, 132, 134, 136, 138, 140, 142, 144, and 146. Sensor substrate 28 appears to stretch after these cuts are made as a result of the deformation of sensor substrate 28 under longitudinal tension.

Cut lines 120-146 are positioned to terminate just adjacent to a corresponding one of the breaks 62-90 as shown. This ensures that as sensor substrate 28 is "stretched" (i.e. deformed under longitudinal tension and extended in length); the major deformation in the form of a compression of the highly resistive element occurs at the corresponding one of the breaks 62-90. This deformation of the graphite providing conductivity across each break produces the resistance change which is measured electrically. The amount of such resistance change indicates the extent of deformation and therefore the amount of longitudinal tension or extension in length.

Because of the natural internal stiffness of substrate 28, the breaks remain closed in the lowest energy state. This state provides one of the extremes in resistance measurement.

Figure 5A:
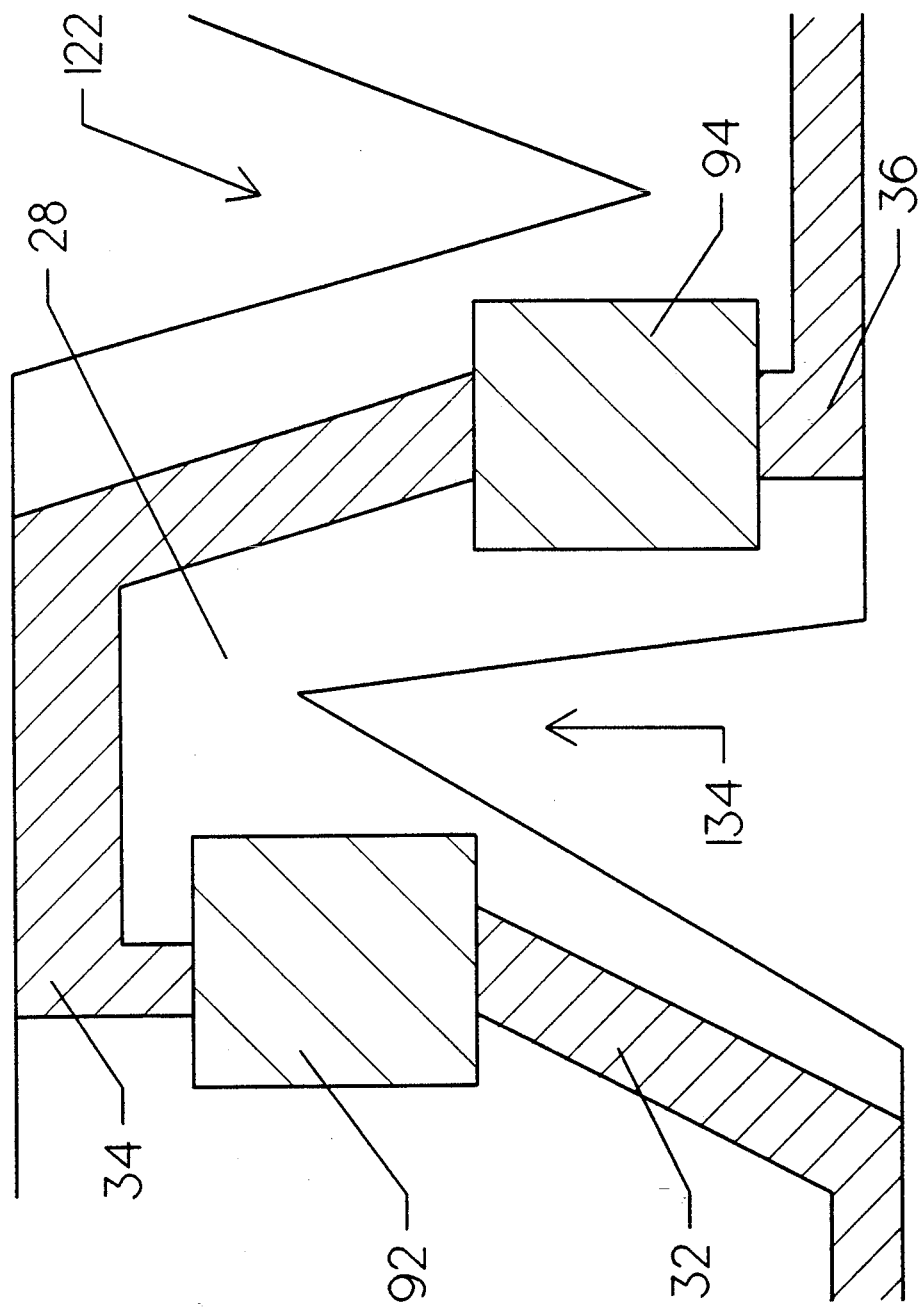
FIG. 5A is a closeup view showing how the resistive area is deformed as the sensor substrate is partially extended.

FIG. 5A is a closeup view of the operation of the strain gauge at two breaks under partial extension of the basic sensor. All referenced elements are as previously described. As longitudinal tension is increased, cuts 134 and 122 are forced open. This imparts a twisting and bending force on resistive pads 92 and 94, respectively. The resulting change in resistance of these and the remaining resistive pads changes the direct current resistance of the strain gauge in accordance with the degree of longitudinal extension.

FIG. 5B is a schematic view of the basic sensor as more fully extended. Further longitudinal tension (see also FIG. 5A) increases the twisting force and further opens the breaks. This continues to elongate the basic sensor.

FIG. 6 is a closeup view of the end of basic sensor structure 20 showing terminal connections. The electrical coupling is provided by sliding connector 157 over the corresponding end of basic sensor 20 as shown. In this way, wire 16 is electrically coupled to segment 150, and wire 14 is electrically coupled to segment 152. Feed through 156 consists of a rivet or other common means to establish electrical contact with the return path on the opposite side of sensor substrate 28 (see above). Wires 14 and 16 are electrically coupled to sliding connector 157 by soldering or other common means.

Figure 7:
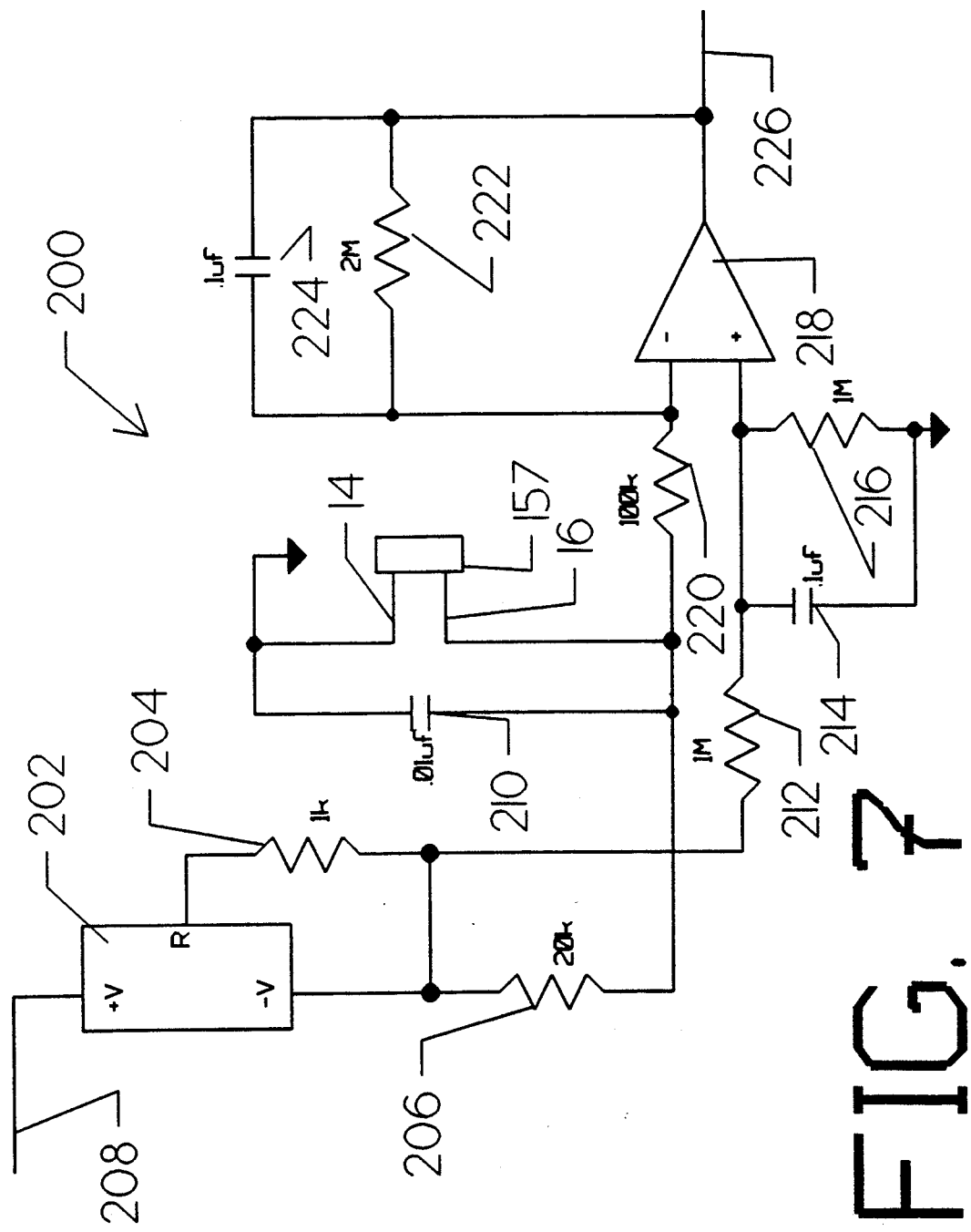
FIG. 7 is an electrical schematic diagram of a typical monitoring circuit.

FIG. 7 is an electrical schematic diagram of a circuit used to monitor resistance variations produced by the basic sensor 20. The circuit is essentially a constant current source in which the varying voltage is observed for changes in sensor resistance.

Constant current device 202 is supplied input power between power input 208 and ground. The current level is set by resistor 204. The negative return to ground is via a resistance bridge consisting of a 20 k ohm series resistor 206 and basic sensor 20, also nominally 20 k, (not shown in this figure) through wires 14 and 16 and sliding connector 157. Parallel capacitor 210 decouples unwanted high frequencies.

The voltage signal representing variations in load experienced by constant current device 202 is amplified by operational amplifier 218 as transferred differentially by series resistors 220 and 212. Differential amplification subtracts out the D.C. voltage allowing high amplification of the small varying voltages without saturating the amplifier. Capacitors 214 and 224 decouple unwanted high frequencies.

Feedback of operational amplifier 218 is provided by capacitor 224 and resistor 222. Output 226 of operational amplifier is an amplified signal with respect to ground which varies as the resistance of basic sensor 20. This signal may be appropriately displayed in linear fashion by a meter or scope to show degree of change of length of basic sensor 20. Alternatively, output 226 may be presented to a bistable device for use as a threshold monitor.

Figure 8:
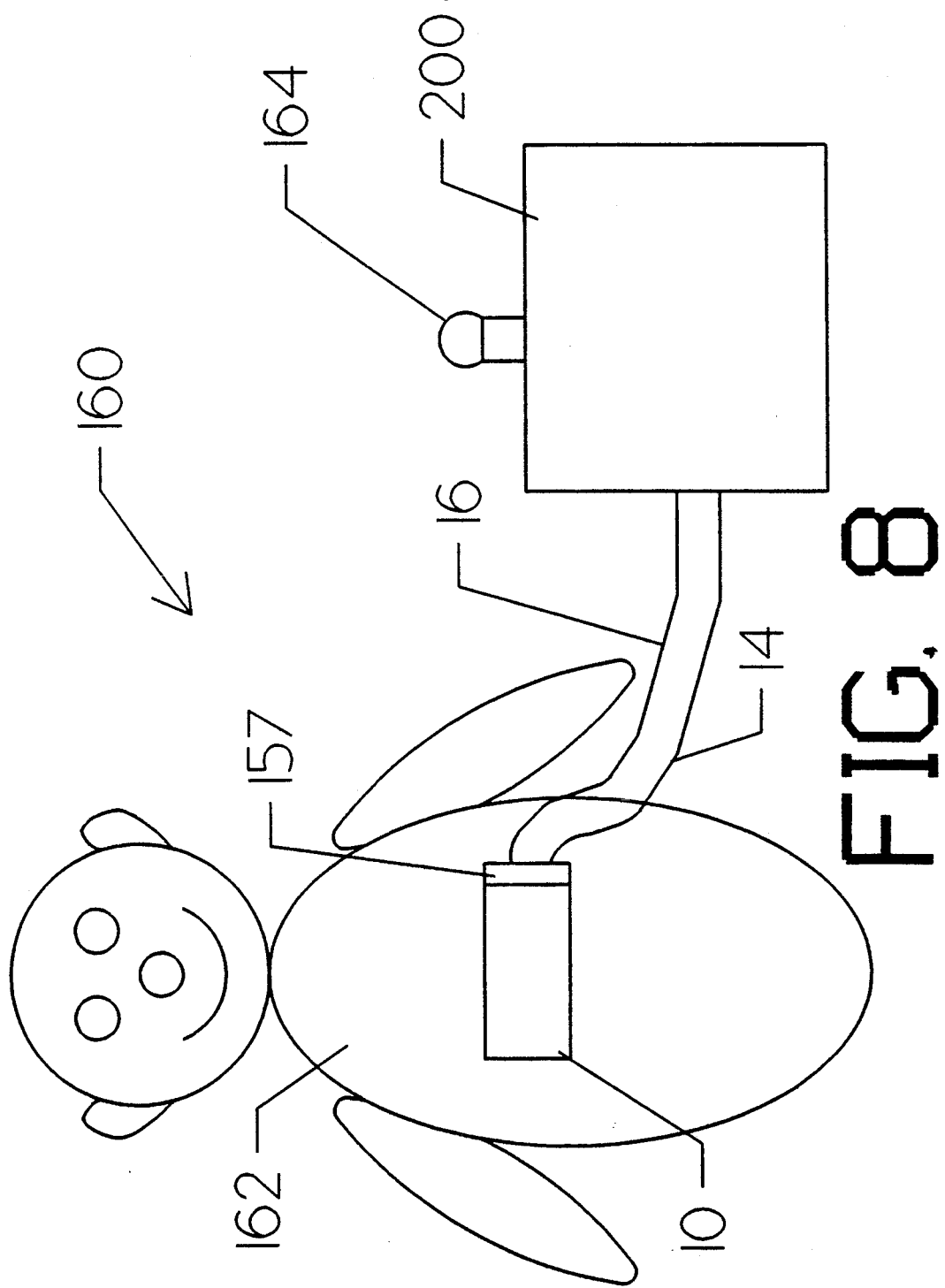
FIG. 8 schematically shows the strain gauge in a typical application for monitoring an apnea patient.

FIG. 8 is a schematic view of a typical application of strain gauge 10 to infant apnea patient 160. Strain gauge 10 is attached to abdomen or thorax 162 of patient 160 as discussed above. Wires 14 and 16 are coupled to electrical circuitry 200 (see also FIG. 7). As patient 160 breathes, abdomen or thorax 162 expands and contracts. This extends and compresses strain gauge 10 causing changes in the voltage measured by electrical circuitry 200. The monitor has a threshold indicator 164 which lights upon an insufficient amount of mechanical activity over a predetermined period of time. This deficiency in mechanical activity is presumed to be central sleep apnea thus necessitating immediate attention to infant apnea patient 160.

Figure 9:
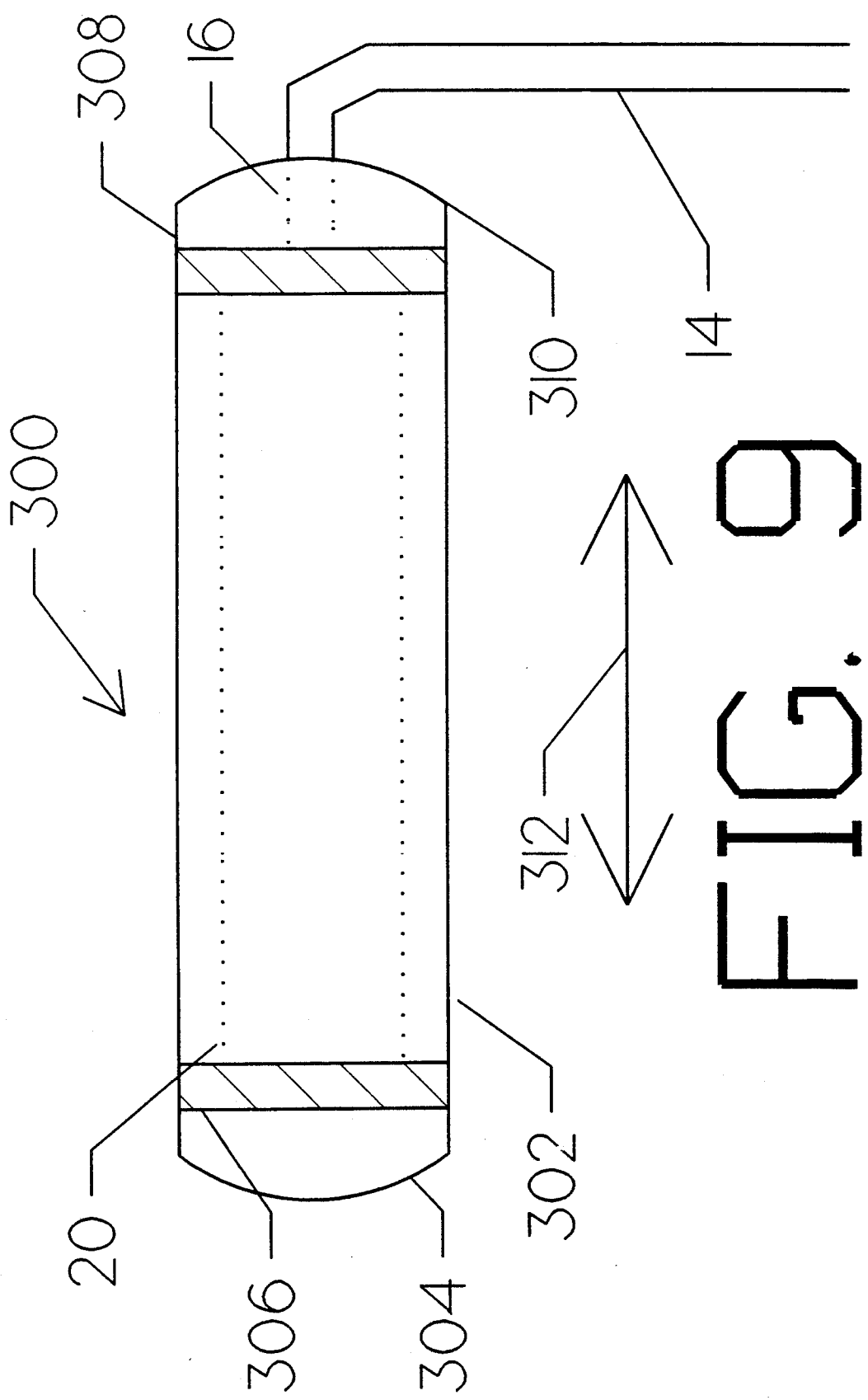
FIG. 9 shows a basic sensor packaged for implantable use.

FIG. 9 is a conceptual view of implantable strain gauge 300 according to the present invention as packaged by chronic implantable use. The device consists primarily of strain gauge 20 encapsulated within an outer protective sheath 302 preferably made of silicone rubber or other elastic biocompatible material. The package is completely sealed at ends 304 and 310 against the ingress of bodily fluids. As with the external mounting (see also FIG. 1), the ends of strain gauge 20 must be fixedly attached to the elastic substrate. In this embodiment, it is convenient to adhesively attach the ends at 306 and 308. In this manner strain gauge 20 is caused to extend and compress along with outer protective sheath 302 in the direction of arrow 312. The remaining referenced elements are as previously described.

Having thus described the preferred embodiments of the present invention, those of skill in the art will be readily able to apply the teachings found herein to yet other embodiments within the scope of the claims hereto attached.

I claim:

1. A strain gauge comprising:
   a. an inelastic substrate;
   b. a path of highly conductive material affixed to said inelastic substrate having a plurality of breaks in conductivity;
   c. a coupling of material at each of said plurality of breaks to complete electrical conductivity of said path which coupling changes an electrical characteristic upon deformation; and
   d. means for causing deformation of said coupling of material at each of said plurality of breaks in response to tension applied to said inelastic substrate.

2. A strain gauge according to claim 1 wherein said causing means comprises a plurality of cuts in said inelastic substrate.

3. A strain gauge according to claim 2 wherein said coupling comprises a plurality of pads of resistive material.

4. A strain gauge according to claim 3 wherein said resistive material comprises graphite.

5. A strain gauge according to claim 4 wherein said highly conductive material has a high content of silver.

6. A strain gauge according to claim 5 wherein said path is applied to a first surface of said inelastic substrate and a return path is applied to a second side of said inelastic substrate.

7. A method of manufacturing a strain gauge comprising:
   a. selecting a substrate of inelastic material;
   b. fixing a path of highly conductive material to said substrate having a plurality of breaks in conductivity;
   c. placing a material of lower conductivity at each of said plurality of breaks in conductivity; and
   d. cutting said substrate in such a manner that tension on said substrate causes said material of lower conductivity to deform.

8. A method according to claim 7 further comprising:
   a. fixedly attaching the ends of said substrate to a second substrate of elastic material.

9. A method according to claim 8 wherein said fixing step comprises silk screening with a conductive ink.

10. A method according to claim 9 further comprising:
    a. fixing a return path to said substrate.

* * * * *